United States Patent [19]

Tosaka et al.

[11] 4,066,501
[45] Jan. 3, 1978

[54] METHOD FOR PRODUCING L-LYSINE BY FERMENTATION

[75] Inventors: Osamu Tosaka, Tokyo; Hajimu Morioka, Kawasaki; Hayao Hirakawa, Yokohama; Kenji Ishii; Koji Kubota, both of Kawasaki; Yoshio Hirose, Fujisawa, all of Japan

[73] Assignee: Ajinomoto Co., Inc., Tokyo, Japan

[21] Appl. No.: 770,692

[22] Filed: Feb. 22, 1977

[30] Foreign Application Priority Data

Feb. 20, 1976 Japan .................................. 51-17518

[51] Int. Cl.² ............................................ C12D 13/06
[52] U.S. Cl. .................................... 195/29; 195/47

[58] Field of Search ...................................... 195/29, 47

[56] References Cited

U.S. PATENT DOCUMENTS 3,707,441 12/1972 Shiio et al. ............................ 195/29
3,905,867 9/1975 Kurimura et al. ...................... 195/29

Primary Examiner—Alvin E. Tanenholtz
Attorney, Agent, or Firm—Cooper, Dunham, Clark, Griffin & Moran

[57] ABSTRACT

L-lysine produced by Brevibacterium or Corynebacterium mutants that are resistant to α-aminolauryllactam, γ-methyl-lysine or N^ω-carbobenzoxy lysine.

4 Claims, No Drawings

METHOD FOR PRODUCING L-LYSINE BY FERMENTATION

This invention relates to a method for producing L-lysine by Fermentation.

L-lysine, which is useful as a feed additive, has been produced by fermentation hitherto.

The inventors have been studying to improve the known process for producing L-lysine, and now have found that a mutant of the genus Brevibacterium or Corynebacterium, which mutant is resistant to one of α-aminolauryllactam (hereinafter referred to as ALL), γ-methyl-lysine (hereinafter referred to as ML) and N$^\omega$-carbobenzoxy-lysine (hereinafter referred to as CBL) can produce L-lysine in higher yield than the known lysine producing mutants.

The specimens of the mutants used in this process are as follows:

Brevibacterium lactofermentum AJ 3985 (FERM-P 3382)
  (CBL$^\gamma$ (resistant to CBL))
Brevibacterium lactofermentum AJ 3986 (FERM-P 3383)
  (ML$^\gamma$)
Brevibacterium lactofermentum AJ 3987 (FERM-P 3384)
  (CBL$^\gamma$, AEC$^\gamma$)
Brevibacterium lactofermentum AJ 3988 (FERM-P 3385)
  (ALL$^\gamma$, AEC$^{65}$)
Brevibacterium lactofermentum AJ 3989 (FERM-P 3386)
  (CBL$^\gamma$, AEC$^\gamma$, Ala$^-$) (requiring alanine for growth))
Brevibacterium lactofermentum AJ 3990 (FERM-P 3387)
  (ML$^{65}$, AEC$^\gamma$, Ala$^-$) (ATCC 31269)
Corynebacterium acetoglutamicum AJ 3983 (FERM-P 3380)
  (CBL$^\gamma$, AEC$^\gamma$) (ATCC 31270)
Corynebacterium acetoglutamicum AJ 3984 (FERM-P 3381)
  (ALL$^\gamma$, AEC$^\gamma$)
Corynebacterium acetoglutamicum AJ 3991 (FERM-P 3414)
  (ML$^\gamma$) (AEC: S-(2-aminoethyl)L-cysteine)

The FERM-P numbers are the accession numbers of the Fermentation Research Institute, Agency of Industrial Science and Technology, at No. 5-2, 4-chome, Inagehigashi, Chiba-shi, Japan, from which the microorganisms having the FERM-P numbers are freely available to any party who requests them.

The ATCC numbers are the accession numbers of American Type Culture Collection, at 12301, Parklawn Drive, Rockville, Md. 20852, U.S.A., from which the microorganisms having the ATCC numbers are also freely available to any party who requests them.

Those lysine producing mutants can be induced, for example, from the following parent strains of the genera Corynebacterium and Brevibacterium.

Brevibacterium divaricatum ATCC 14020
Brevibacterium flavum ATCC 14067
Brevibacterium lactofermentum ATCC 13869
Brevibacterium roseum ATCC 13825
Corynebacterium acetoacidophilum ATCC 13870
Corynebacterium acetoglutamicum ATCC 15806
Micrococcus glutamicus ATCC 13032
  (Corynebacterium glutamicum)

Those parent strains have the following common characteristics:

1. They are known as L-glutamic acid producing microorganisms, and all of them belong to so-called Coryne-form bacteria.
2. Mutants induced from the parent strains are known to produce L-lysine.
3. The growth of the parent strains is inhibited by the addition of ALL, ML or CBL in the medium, and the growth inhibition is suppressed by the presence of L-lysine in the same medium. This means clearly that all of the mutant induced from the parent strains and resistant to ALL, ML or CBL can produce L-lysine.

Methods for inducing and separating the mutants of this invention are conventional. The following experiment shows an example of the methods for inducing and separating the mutants.

EXPERIMENT

Brevibacterium lactofermentum ATCC 13869 was exposed to 250 μg/ml N-methyl-N'-nitro-N-nitrosoguanidine at 30° C for 30 minutes. The exposed strains are spread on the agar plate medium mentioned below and cultured for 4 to 10 days at 30° C.

| Medium | |
|---|---|
| glucose | 2 g/dl |
| urea | 0.3 g/dl |
| $(NH_4)_2SO_4$ | 1 g/dl |
| $KH_2PO_4$ | 0.1 g/dl |
| $MgSO_4 \cdot 7H_2O$ | 0.04 g/dl |
| $FeSO_4 \cdot 7H_2O$ | 1 mg/dl |
| $MnSO_4 \cdot 4H_2O$ | 1 mg/dl |
| biotin | 50 μg/l |
| thiamine . HCl | 100 μg/l |
| CBL | 0.1 g/dl |
| agar | 2 g/dl |

Colonies formed on the plate medium were separated, and from the colonies, the most effective lysine-producing mutant AJ 3985 was separated.

Other mutants of this invention were induced by the analogous mutation method as mentioned above.

The microorganisms are cultured on Medium A at 30° C for 24 hours, and cells grown on the medium were collected, washed with Medium B, and thereafter suspended in Medium B.

| Medium A | |
|---|---|
| yeast extract | 1 g/dl |
| peptone | 1 g/dl |
| NaCl | 0.5 g/dl |
| glucose | 0.5 g/dl |
| agar | 2.0 g/dl |
| | (pH 7.0) |
| Medium B | |
| glucose | 2 g/dl |
| $(NH_4)_2SO_4$ | 1 g/dl |
| $KH_2PO_4$ | 0.1 g/dl |
| $MgSO_4 \cdot 7H_2O$ | 0.04 g/dl |
| $FeSO_4 \cdot 7H_2O$ | 1 mg/dl |
| biotin | 50 μg/l |
| thiamine . HCl | 200 μg/l |
| NaCl | 0.05 g/dl |
| $CaCO_3$ (separately sterilized) | 3 g/dl |
| $MnSO_4 \cdot 7H_2O$ | 1 mg/dl |

Each 0.1 ml of the cells suspension was inoculated into 3 ml of Medium B containing the amounts of ALL, CBL or ML, and the microorganisms were cultured in 10 ml test tube at 30° C for 20 hours with shaking.

After the cultivation, growth was determined by measuring the optical density at 562 mµ of the culture broth diluted to 26 times. The results are shown in Table 1.

The mutants thus obtained can produce large amounts of L-lysine in their culture medium, even when the mutant only have the characteristics of resistance to ALL, ML or CBL. However, when they have additional characteristics which are known to contribute to increase the yield of L-lysine such as resistance to AEC, or alanine-requirement, the productivity of L-lysine is remarkably increased usually.

The methods for producing L-lysine using the microorganisms mentioned above are conventional, and the microorganisms are cultured in a conventional medium containing carbon sources, nitrogen sources, inorganic salts, nutrients required for growth, and other minor nutrients.

As the carbon source, carbohydrates such as glucose, sucrose, molasses, or starch hydrolyzate, organic acids such as acetic acid, propionic acid, or benzoic acid, alcohols such as ethanol, or propanol and for a certain strains hydrocarbons can be used. As the nitrogen source, ammonia, ammonium sulfate, ammonium nitrate, ammonium phosphate, urea, and so on, can be used.

Nutrients required for growth can be used as a purified ones, or as a natural substances containing the nutrients such as soybean-hydrolyzate, corn steep liquor, yeast extract or peptone.

Cultivation is carried out under aerobic conditions at a temperature of from 24° to 37° C, for 2 to 7 days. During the cultivation the pH of the medium is adjusted to 5 to 9 by alkali or acid, or calcium carbonate, urea or gaseous ammonia.

L-lysine in the culture broth thus obtained can be separated by known methods such as by using ion-exchange resins, or by directly crystallizing L-lysine from the culture broths.

EXAMPLE 1

The culture medium mentioned below (20 ml) was placed in 500 ml shaking flasks, and heated at 110° C for 5 minutes.

| Culture Medium | |
|---|---|
| glucose | 10 g/dl |
| ammonium sulfate | 5 g/dl |
| $KH_2PO_4$ | 0.1 g/dl |
| $MgSO_4 . 7H_2O$ | 0.04 g/dl |
| $FeSO_4 . 7H_2O$ | 1.0 mg/dl |
| $MnSO_4 . 4H_2O$ | 1.0 mg/dl |
| biotin | 5.0 µg/dl |
| thiamine . HCl | 20.0 µg/dl |
| soybean-hydrolyzate (total nitrogen contained being 7%) | 1.5 ml/dl |
| calcium carbonate (separately sterilized) | 5 % |
| (pH 7.0) | |

Each of the microorganisms shown in Table 2 was inoculated in the culture medium, and the culture medium was held at 31° C for 72 hours with shaking.

After the cultivation, the amount of L-lysine in the resultant culture medium was determined, and is shown in Table 2 as the amount of L-lysine hydrochloride.

EXAMPLE 2

Corynebacterium acetoglutamicum AJ 3983, AJ 3984, AJ 3991 or ATCC 21491 (AECγ) was cultured in the analogous manner to EXAMPLE 1, and produced L-lysine in the respective culture media in the amounts of 25 g/l, 24 g/l, 3.0 g/l and 15 g/l, respectively.

EXAMPLE 3

The microorganisms shown in Table 3 were cultured aerobically in the following seed culture medium of 50 ml at 31° C for 18 hours.

| Seed culture medium | |
|---|---|
| glucose | 1.5 g/dl |
| ammonium acetate | 0.3 g/dl |
| urea | 0.1 g/dl |
| $KH_2PO_4$ | 0.1 g/dl |
| $MgSO_4 . 7H_2O$ | 0.04 g/dl |
| $FeSO_4 . 7H_2O$ | 1 mg/dl |
| $MnSO_4 . 4H_2O$ | 1 mg/dl |
| biotin | 50 µg/l |
| thiamine . HCl | 200 µg/l |
| soybean-hydrolyzate (total nitrogen contained being 7%) | 3 ml/dl |
| (pH 7.5) | |

Three hundreds portions of the following culture medium were placed in 1 liter fermentation vessels, heated, and inoculated with 15 ml of the seed culture broth mentioned above.

| Culture medium | |
|---|---|
| glucose | 2 g/dl |
| ammonium acetate | 0.5 g/dl |
| urea | 0.2 g/dl |
| $(NH_4)_2SO_4$ | 0.5 g/dl |
| $KH_2PO_4$ | 0.1 g/dl |
| $MgSO_4 . 7H_2O$ | 0.04 g/dl |
| $FeSO_4 . 7H_2O$ | 1 mg/dl |
| $MnSO_4 . 7H_2O$ | 1 mg/dl |
| biotin | 50 µg/l |
| thiamine . HCl | 60 µg/l |
| soybean-hydrolyzate | 3 ml/dl |
| (pH 7.5) | |

Cultivation was carried out aerobically at 30° C. During the cultivation, a small portion of an aqueous solution containing acetic acid and ammonium acetate was fed to the culture medium so as to maintain the pH of the medium to 7.2 to 8.0.

After 72 hours cultivation, the amounts of L-lysine shown in Table 3 were accumulated in the resultant culture medium.

EXAMPLE 4

The microorganisms shown in Table 4 were cultured aerobically at 31° C for 18 hours in 50 ml of the same seed culture medium as shown in Example 3 except that 0.5 g/dl ethylalcohol and 0.3 g/dl urea were added in place of 0.3 g/dl ammonium acetate and 0.1 g/dl urea.

Meanwhile, 300 ml portions of the same culture medium as shown in Example 3 except that glucose concentration was 1 g/dl, and 1 g/dl ethylalcohol was added in place of 0.5 g/dl ammonium acetate were placed in 1 liter fermentation vessels, and heated. The culture medium was inoculated with 15 ml of the seed culture broth mentioned above, and cultured aerobically at 31° C.

During the cultivation, the pH of the medium was adjusted to 7.2 to 8.2 with gaseous ammonia. The concentration of ethylalcohol in the culture medium was determined from time to time by gas-chromatography, and the concentration was maintained at about 0.3 g/dl by feeding ethylalcohol.

After 56 hours cultivation, the amounts of L-lysine shown in Table 4 were found in the respective culture medium.

EXAMPLE 5

The following culture medium was prepared, and 20 ml portions of the culture medium were placed in 500 ml shaking flasks, and heated.

| Culture medium | |
|---|---|
| beet molasses or cane molasses | 10 g/dl (as glucose) |
| ammonium sulfate | 5 g/dl |
| KH$_2$PO$_4$ | 0.1 g/dl |
| MgSO$_4$ . 7H$_2$O | 0.04 g/dl |
| biotin | 0.5 mg/l |
| CaCO$_3$ (separately sterilized) | 5 g/dl |

The culture medium was innoculated with the microorganisms shown in Table 5, and held at 30° C for 72 hours with shaking.

The resultant culture media contained the amounts of L-lysine shown in Table 5.

One liter of cultured broth was prepared by culturing AJ 3989 by the analogous manner as above, and the culture broth was centrifuged to remove cells, and the supernatant was passed through a strongly acidic ion exchange resin "Amberlite 1R-120."The absorbed L-lysine on the resin was eluted with 3% ammonia water, and from the eluate, crystals of L-lysine hydrochloride two hydrates were recovered (28.5 g).

TABLE 1

| Microorganism | Chemicals added | Amount of Chemicals added (%) | Relative growth (%) |
|---|---|---|---|
| ATCC 13869 (note 1) | none | — | 100 |
| | CBL | 0.1 | 21 |
| | ML | 0.1 | 9 |
| | ALL | 0.025 | 12 |
| AJ 3985 | none | — | 100 |
| | CBL | 0.1 | 79 |
| AJ 3986 | none | — | 100 |
| | ML | 0.1 | 96 |
| AJ 3987 | none | — | 100 |
| | CBL | 0.1 | 94 |
| AJ 3988 | none | — | 100 |
| | ALL | 0.025 | 58 |
| AJ 3989 (note 2) | none | — | 100 |
| | CBL | 0.1 | 82 |
| AJ 3990 (note 2) | none | — | 100 |
| | ML | 0.1 | 79 |
| ATCC 15806 (note 3) | none | — | 100 |
| | CBL | 0.1 | 26 |
| | ML | 0.1 | 19 |
| | ALL | 0.01 | 6 |
| AJ 3991 | none | — | 100 |
| | ML | 0.1 | 95 |
| AJ 3983 | none | — | 100 |
| | CBL | 0.1 | 93 |
| AJ 3984 | none | — | 100 |
| | ALL | 0.01 | 47 | note 1: ATCC 13869 is the parent strain of AJ 3985, AJ 3986, AJ 3987, AJ 3988, AJ 3989 and AJ 3990.
note 2: AJ 3989 and AJ 3990 were cultured in Medium B further containing 500 μg/ml L-alanine and 5 μg/ml nicotineamide.
note 3: ATCC 15806 is the parent strain of AJ 3991, AJ 3983 and AJ 3984.

TABLE 2

| | L-lysine accumulated (g/l) |
|---|---|
| AJ 3985 | 2.0 |
| AJ 3986 | 1.5 |
| AJ 3987 | 27 |
| AJ 3988 | 28 |
| AJ 3989 | 37 |
| AJ 3990 | 36 |
| AJ 3445 | 18 |

AJ 3445 (AECγ) is an L-lysine producing mutant of Brevibacterium lactofermentum, which does not have the resistance to CBL, ML or ALL.

TABLE 3

| Microorganism | L-lysine accumulated (g/l) |
|---|---|
| AJ 3988 | 85 |
| AJ 3989 | 96 |
| AJ 3990 | 94 |
| AJ 3445 | 41 |

TABLE 4

| Microorganism | L-lysine accumulated (g/l) | Yield of L-lysine per ethylalcohol consumed (%) |
|---|---|---|
| AJ 3988 | 63 | 24 |
| AJ 3989 | 83 | 32 |
| AJ 3990 | 78 | 30 |
| AJ 3445 | 36 | 17 |

TABLE 5

| | L-lysine accumulated (g/l) | |
|---|---|---|
| Microorganism | Beet molasses | Cane molasses |
| AJ 3445 | 20 | 19 |
| AJ 3987 | 27 | 27 |
| AJ 3988 | 30 | 29 |
| AJ 3989 | 39 | 37 |
| ATCC 21491 | 20 | 18 |
| AJ 3983 | 26 | 23 |
| AJ 3984 | 27 | 25 |

What is claimed is:
1. A method for producing L-lysine by fermentation which comprises:
   a. aerobically culturing in an aqueous culture medium an L-lysine producing mutant belonging to the genus Brevibacterium or Corynebacterium until L-lysine is accumulated in the culture medium, said mutant being resistant to α-amino-lauryllactam, α-methyl-lysine, or N$^\omega$-carbobenzoxy-lysine;
   b. recovering the accumulated L-lysine from the culture medium.

2. A method as set forth in claim 1, wherein said mutant is additionally resistant to S-(2-aminoethyl)-L-cysteine.

3. A method as set forth in claim 2, wherein said mutant additionally requires L-alanine for growth.

4. A method as set forth in claim 1, wherein said mutant is:

Brevibacterium lactofermentum FERM-P 3382
Brevibacterium lactofermentum FERM-P 3383
Brevibacterium lactofermentum FERM-P 3384
Brevibacterium lactofermentum FERM-P 3385
Brevibacterium lactofermentum FERM-P 3386
Brevibacterium lactofermentum FERM-P 3387 (ATCC 31269)
Corynebacterium acetoglutamicum FERM-P 3380 (ATCC 31270)
Corynebacterium acetoglutamicum FERM-P 3381 or
Corynebacterium acetoglutamicum FERM-P 3414.

* * * * *

UNITED STATES PATENT AND TRADEMARK OFFICE
CERTIFICATE OF CORRECTION

PATENT NO. : 4,066,501

DATED : January 3, 1978

INVENTOR(S) : TOSAKA ET AL.

It is certified that error appears in the above-identified patent and that said Letters Patent is hereby corrected as shown below:

In column 6, line 47, "α-methyl-lysine" should read -- γ-methyl-lysine --.

Signed and Sealed this

Nineteenth Day of January, 1993

*Attest:*

DOUGLAS B. COMER

*Attesting Officer*     *Acting Commissioner of Patents and Trademarks*